United States Patent
Naser et al.

(10) Patent No.: US 10,285,920 B2
(45) Date of Patent: May 14, 2019

(54) EXTENDED RELEASE FRAGRANCE COMPOSITIONS

(71) Applicant: Avon Products, Inc., Suffern, NY (US)

(72) Inventors: Mark S. Naser, Franklin, NJ (US); Andrew H. Pechko, Ridgewood, NJ (US)

(73) Assignee: Avon Products, Inc., Suffern, NY (US)

( * ) Notice: Subject to any disclaimer, the term of this patent is extended or adjusted under 35 U.S.C. 154(b) by 0 days.

(21) Appl. No.: 14/990,098

(22) Filed: Jan. 7, 2016

(65) Prior Publication Data

US 2017/0196786 A1    Jul. 13, 2017

(51) Int. Cl.

| | | |
|---|---|---|
| *A61K 8/37* | (2006.01) | |
| *A61Q 15/00* | (2006.01) | |
| *A61K 8/97* | (2017.01) | |
| *A61K 8/34* | (2006.01) | |
| *A61K 8/06* | (2006.01) | |
| *A61Q 7/02* | (2006.01) | |
| *A61Q 19/02* | (2006.01) | |
| *A61K 8/28* | (2006.01) | |
| *A61Q 19/00* | (2006.01) | |
| *A61Q 13/00* | (2006.01) | |
| *A45D 34/04* | (2006.01) | |

(52) U.S. Cl.
CPC ............ *A61K 8/375* (2013.01); *A45D 34/041* (2013.01); *A61K 8/062* (2013.01); *A61K 8/28* (2013.01); *A61K 8/345* (2013.01); *A61K 8/97* (2013.01); *A61Q 7/02* (2013.01); *A61Q 13/00* (2013.01); *A61Q 15/00* (2013.01); *A61Q 19/007* (2013.01); *A61Q 19/02* (2013.01); *A61K 2800/31* (2013.01); *A61K 2800/522* (2013.01); *A61K 2800/524* (2013.01); *A61K 2800/596* (2013.01); *A61K 2800/874* (2013.01)

(58) Field of Classification Search
CPC .......... A61K 8/375; A61K 8/062; A61K 8/28; A61K 8/345; A61K 8/97; A61K 2800/874; A61K 2800/31; A61K 2800/596; A61K 2800/524; A61K 2800/522; A61Q 13/00; A61Q 19/007; A61Q 7/02; A61Q 15/00; A61Q 19/02; A45D 34/041

See application file for complete search history.

(56) References Cited

U.S. PATENT DOCUMENTS

| | | |
|---|---|---|
| 7,238,343 B2 | 7/2007 | Lee et al. |
| 2004/0247545 A1 | 12/2004 | Jonas et al. |
| 2006/0029624 A1 | 2/2006 | Banowski et al. |
| 2006/0115541 A1 | 6/2006 | Gillis et al. |
| 2009/0317347 A1 | 12/2009 | Popoff et al. |
| 2010/0047296 A1* | 2/2010 | Banowski ............ A61K 8/0229 424/401 |
| 2011/0076309 A1 | 3/2011 | Misner et al. |
| 2011/0076310 A1 | 3/2011 | Fan et al. |
| 2012/0014896 A1 | 1/2012 | Dombeck |
| 2013/0189208 A1* | 7/2013 | Bianchi .................. A61Q 15/00 424/65 |
| 2013/0280409 A1 | 10/2013 | Mushock et al. |

FOREIGN PATENT DOCUMENTS

| | | |
|---|---|---|
| CA | 2773164 A1 | 4/2011 |
| EP | 0274267 B1 | 7/1992 |
| EP | 2201926 A1 | 6/2010 |
| EP | 2229932 A1 | 9/2010 |
| EP | 2415449 A2 | 2/2012 |
| EP | 2481392 A2 | 8/2012 |
| WO | 2002102337 A1 | 12/2002 |
| WO | 2011/134747 A | 11/2011 |
| WO | 2012084422 A2 | 6/2012 |
| WO | 2013160065 A1 | 10/2013 |

OTHER PUBLICATIONS

"Tinogard TT Technical Information" (BASF SE) Feb. 2011; p. 2 characterization, p. 3 applications.
www.thecoconut-----.com/coconut-oil-deodorant.

* cited by examiner

*Primary Examiner* — Robert S Cabral
(74) *Attorney, Agent, or Firm* — Brian P. McCloskey

(57) ABSTRACT

Compositions are provided that provide fragrance over an extended period of time. The compositions comprise a fragrance and one or more other ingredients.

17 Claims, No Drawings

EXTENDED RELEASE FRAGRANCE COMPOSITIONS

FIELD OF INVENTION

The invention relates generally to scented antiperspirant compositions comprising one or more fragrance oils dispersed in an oil phase, which are characterized by a reduced loss of fragrance character and intensity over time.

BACKGROUND OF THE INVENTION

Antiperspirant compositions are commonly applied to skin, such as the underarms, to prevent or reduce body sweating and/or odor. Such compositions take a variety of physical forms including sticks, soft solids, gels, creams, roll-on liquids, or pump or aerosol sprays. Antiperspirant compositions also typically contain fragrance to enhance the smell of the personal care product, mask or eliminate body odor, or provide other functional benefits, such as repelling insects.

However, the fragrance character and intensity of many antiperspirant compositions degrades or deteriorates rapidly over time on storage. Attempts have been made to mitigate the loss of perfume fragrance on storage by introducing various stabilizing agents into antiperspirant compositions. (See, e.g., EP0274267) Other methods for combating loss of fragrance have involved incorporating antioxidants, elevating fragrance levels, and reformulating commercially available fragrance oils.

There remains a need in the art for compositions, including antiperspirants, having a reduced loss of fragrance character and intensity over time, preferably provided without necessarily increasing the fragrance load, or requiring specialized fragrances or stabilizers.

It is therefore an object of the invention to provide compositions that provide reduced loss of fragrance levels on storage, both in terms of character and intensity, in an antiperspirant composition, and packaged personal care products containing such compositions.

The foregoing discussion is presented solely to provide a better understanding of the nature of the problems confronting the art and should not be construed in any way as an admission as to prior art nor should the citation of any reference herein be construed as an admission that such reference constitutes "prior art" to the instant application.

SUMMARY OF THE INVENTION

In accordance with the foregoing objectives and others, antiperspirant compositions are provided that provide stable fragrance character and intensity over prolonged storage periods. It has surprisingly been found that antiperspirant compositions comprising one or more fragrance oils dispersed in an oil phase comprising one or more triglyceride oils collectively having a saturated fatty acid content of at least 75%, provide reduced loss of fragrance character and intensity over time as compared to otherwise identical formulations having lesser saturated fatty acid content. The antiperspirant compositions ideally provide one or more other desirable benefits, such as exhibiting a soft feel to the skin when applied, moisturizing the skin, reducing of whitening effect of inorganic antiperspirant actives on the skin, reducing skin irritancy and/or darkening, and evening out skin tone.

The compositions are typically in the form of emulsions (e.g., oil-in-water or water-in-oil) or dispersions in water or alcohol, such as in a roll-on antiperspirant, but may also take the form of a cream, gel, soft solid, stick, or spray, for example. In one aspect of the invention, the compositions may comprise one or more fragrance oils in an amount, individually or in the aggregate, of from about 0.1% to about 3% by weight (e.g., about 0.5%, 1%, 1.5%, 2%, or about 2.5%) of the composition. The fragrance oil may be an oil that is used for primarily aesthetic benefits (e.g., a perfume), functional benefits (e.g., an insect repellant such as citronella oil), or both. The compositions may also comprise an oil phase. The oil phase is typically present in the composition in an amount of from about 0.1% to about 20% by weight, more typically from about 1 to about 10%, or from about 2 to about 8% by weight. The oil phase is typically comprised of one or more triglyceride oils which collectively have a saturated fatty acid content of at least 75% or more (e.g., of at least 80%, 85%, 90%, 95%, etc.) by weight, such as coconut oil or palm kernel oil. Typically the fatty acid content of the oil phase comprises at least 75% of fatty acids having a chain length of C16 or less. In some embodiments, the oil phase of the compositions comprise less than 5%, 4%, 3%, or 2% by weight, or is substantially free of (i.e., less than 1% by weight), or free of, oils having a relatively high unsaturated fatty acid content (i.e., greater than 25%), such as sunflower seed oil, rapeseed oil, corn oil, cottonseed oil, flaxseed oil, olive oil, safflower oil, soybean oil, canola oil, peanut oil, sesame oil, almond oil, castor oil, and combinations thereof. The compositions may further comprise one or more antiperspirant actives, which may reduce or eliminate body sweat, in an amount from about 1 to about 25% (e.g., about 5-15%) by weight of the composition on an anhydrous solids basis. Preferably such antiperspirant actives are aluminum-based or an aluminum/zirconium-based. For example, the one or more antiperspirant actives may be aluminum salts or aluminum/zirconium salts, aluminum or aluminum/zirconium glycol complexes, and/or combinations thereof. The compositions may further comprise a polyol, preferably glycerol, for example, in an amount of about 0.1 to about 25% by weight, more typically about from about 1 to about 10% by weight of the composition. The compositions are typically aqueous, though they may be substantially anhydrous or anhydrous. Aqueous compositions may contain at least 1% water but typically will comprise water in an amount of from about 20-95% or from about 50-90% by weight (e.g., about 60%, 70%, 80%, etc.) of the composition.

The compositions of the invention may optionally comprise additional ingredients, such as one or more of emollients, humectants, preservatives, chelating agents, antioxidants, solvents, rheology modifiers, pH adjusters, skin conditioners, emulsifiers, stabilizers, film formers, sunscreens, colorants (e.g., pigments, lakes, dyes, etc.), botanical extracts, or other ingredients which may render the compositions functional or beneficial to skin (e.g., antibacterial s, anti-fungal s, etc.).

In another aspect of the invention, a packaged personal care product is provided comprising a container in which is disposed a liquid composition according to the invention, and a roll-on applicator for delivering an amount of the composition to an integument of a user. In other embodiments, packaged personal care products are provided comprising a container having a composition according to the invention contained therein, the composition being in the form of a solid or gel, and a means for advancing said composition from an open orifice of said container.

These and other aspects of the present invention will become apparent to those skilled in the art after a reading of the following detailed description of the invention, including the appended claims.

DETAILED DESCRIPTION

All amounts provided in terms of weight percentage are relative to the entire composition unless otherwise stated. It will be understood that the total of all weight percentages in a given composition will not exceed 100%. Unless otherwise specified, any components of the compositions of the invention may be included in an amount from about 0.0001% to about 25% by weight of the composition, including amounts from about 0.001-20% by weight, or 0.01-10% by weight, or from 0.05-5% by weight, or from 0.1-1% by weight. All ingredients are preferably "physiologically acceptable," by which is meant safe and non-irritating, at the levels employed.

The antiperspirant compositions of the invention typically comprise a fragrance oil and an oil phase. The fragrance oil is usually dissolved or dispersed in the oil phase. The oil phase has a low content of unsaturated fatty acids and will typically comprise one or more vegetable triglyceride oils collectively having 75% or more of the fatty acids constituted by saturated fatty acids.

Fragrance

The compositions of the invention comprise one or more fragrance oils. The fragrance oils typically comprise from about 0.1% to about 3% by weight (e.g., about 0.5%, 1%, 1.5%, 2%, 2.5% by weight) of the composition. In one embodiment, the one or more fragrance oils individually or in the aggregate comprise about 1-2% or about 1.5% by weight of the composition.

Any fragrance oil can be used in the compositions of the invention, such as those described in U.S. Patent Application Publication No. 2013/0280409, hereby incorporated by reference in its entirety. For example, the fragrance oil may include any one or more of extracts of natural raw materials such as essential oils, concretes, absolutes, resins, resinoids, balsams, tinctures such as, for example, ambergris tincture; amyris oil; *angelica* seed oil; *angelica* root oil; aniseed oil; valerian oil; basil oil; wood moss absolute; bay oil; mugwort oil; benzoin resin; bergamot oil; beeswax absolute; birch tar oil; bitter almond oil; savory oil; bucco-leaf oil; cabreuva oil; cade oil; calamus oil; camphor oil; *cananga* oil; cardamom oil; cascarilla oil; *cassia* oil; *cassia* absolute; castoreum absolute; cedar-leaf oil; cedarwood oil; cistus oil; citronella oil; lemon oil; copaiba balsam; copaiba balsam oil; coriander oil; costus root oil; cumin oil; cypress oil; davana oil; dill oil; dillseed oil; eau de brouts absolute; oakmoss absolute; elemi oil; tarragon oil; *eucalyptus citriodora* oil; *eucalyptus* oil; fennel oil; fir oil; *galbanum* oil; *galbanum* resin; geranium oil; grapefruit oil; guaiac wood oil; gurjun balsam; gurjun balsam oil; helichrysum absolute; helichrysum oil; ginger oil; iris root abolute; iris root oil; jasmine absolute; calamus oil; blue camomile oil; Roman camomile oil; carrot-seed oil; cascarilla oil; pine-needle oil; spearmint oil; caraway oil; labdanum oil; labdanum absolute; labdanum resin; lavandin absolute; lavandin oil; lavender absolute; lavender oil; lemongrass oil; lovage oil; distilled lime oil; pressed lime oil; linaloe oil; *litsea cubeba* oil; bay-leaf oil; mace oil; marjoram oil; mandarin oil; massoi bark oil; *mimosa* absolute; ambrette oil; tincture of musk; clary sage oil; *myristica* oil; myrrh absolute; myrrh oil; myrtle oil; clove leaf oil; clove flower oil; neroli oil; olibanum abolute; olibanum oil; opopanax oil; orange blossom absolute; orange oil; *origanum* oil; palmarosa oil; patchouli oil; *perilla* oil; Peru balsam oil; parsley leaf oil; parsley seed oil; petitgrain oil; peppermint oil; pepper oil; pimento oil; pine oil; pennyroyal oil; rose absolute; rosewood oil; rose oil; rosemary oil; Dalmatian sage oil; Spanish sage oil; sandalwood oil; celery seed oil; spike lavender oil; Japanese aniseed oil; *styrax* oil; *tagetes* oil; fir-needle oil; tea-tree oil; turpentine oil; thyme oil; Tolu balsam; tonka absolute; tuberose absolute; vanilla extract; violet leaf absolute; *verbena* oil; vetiver oil; juniper oil; wine-lees oil; wormwood oil; wintergreen oil; ylang oil; hyssop oil; civet absolute; cinnamon leaf oil; cinnamon bark oil; as well as fractions thereof or constituents isolated therefrom; and combinations thereof.

Additional suitable fragrances, as listed in European Patent No. EP2106704B1, include, for example, any one or more of hydrocarbons, such as 3-carene; α-pinene; β-pinene; α-terpinene; γ-terpinene; p-cymene; bisabolene; camphene; caryophyllene, cedrene; farnesene; liminene; longifolene; myrcene; ocimene; valencene; (E,Z)-1,3,5-undecatriene;

Aliphatic alcohols, such as hexanol; octanol; 3-octanol; 2,6-dimethylheptanol; 2-methylheptanol; 2-methyloctanol; (E)-3-hexenol; (E) and (Z)-3-hexenol; 1-octen-3-ol; mixtures of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

Aliphatic aldehydes and their acetals, such as hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal diethyl acetal; 1,1-dimethoxy-2,2,5-trimethyl-4-hexene; citronellyl oxyacetaldehyde;

Aliphatic ketones and oximes thereof, such as 2-heptanone; 2-octanone; 3-octanone; 2-nonanone; 5-methyl-3-heptanone; 5-methyl-3-heptanone oxime; 2,4,4,7-tetramethyl-6-octen-3-one;

Aliphatic sulphur-containing compounds, such as 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

Aliphatic nitriles, such as 2-nonenenitrile; 2-tridecenenenitrile; 2,12-tridecenene-nitrile; 3,7-dimethyl-2,6-octadienenitrile; 3,7-dimethyl-6-octenenitrile;

Aliphatic carboxylic acids and esters thereof, such as (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octynoate; methyl 2-nonynoate; allyl-2-isoamyloxyacetate; methyl-3,7-dimethyl-2,6-octadienoate;

Acyclic terpene alcohols, such as citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and formates, acetates, propionates, isobutyrates, butyrates, isovalerates, pentanoates, hexanoates, crotonates, tiglinates, 3-methyl-2-butenoates thereof;

Acyclic terpene aldehydes and ketones, such as geranial; neral; citronellal; 7-hydroxy-3,7-dimethyloctanal; 7-methoxy-3,7-dimethyloctanal; 2,6,10-trimethyl-9-undecenal; geranylacetone; and the dimethyl and diethyl acetals of geranial, neral, 7-hydroxy-3,7-dimethyloctanal;

Cyclic terpene alcohols, such as menthol; isopulegol; alpha-terpineol; terpineol-4; menthan-8-ol; menthan-1-ol; menthan-7-ol; borneol; isoborneol; linalool oxide; nopol; cedrol; ambrinol; vetiverol; guaiol; and the formates, acetates, propionates, isobutyrates, butyrates, isovalerates, pentanoates, hexanoates, crotonates, tiglinates, 3-methyl-2-butenoates thereof;

Cyclic terpene aldehydes and ketones, such as menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; nootkatone; dihydronootkatone; alpha-sinensal; beta-sinensal; acetylated cedarwood oil (methyl cedryl ketone);

Cyclic alcohols, such as 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

Cycloaliphatic alcohols, such as alpha-3,3-trimethylcyclohexylmethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

Cyclic and cycloaliphatic ethers, such as cineol; cedryl methyl ether; cyclododecyl methyl ether; (ethoxymethoxy)cyclododecane; alpha-cedrene epoxide; 3a,6,6,9a-tetramethyl-dodecahydronaphtho[2,1-b]furan; 3a-ethyl-6,6,9a-trimethyldodecahydro-naphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

Cyclic ketones, such as 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 9-cycloheptadecen-1-one; cyclopentadecanone; cyclohexadecanone;

Cycloaliphatic aldehydes, such as 2,4-dimethyl-3-cyclohexenecarbaldehyde; 2-methyl-4-(2,2,6-trimethyl-cyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

Cycloaliphatic ketones, such as 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl-2,6,10-trimethyl-2,5,9-cyclododecatrienyl ketone; tert.-butyl (2,4-dimethyl-3-cyclohexen-1-yl) ketone;

Esters of cyclic alcohols, such as 2-tert.-butylcyclohexyl acetate; 4-tert.-butylcyclohexyl acetate; 2-tert.-pentylcyclohexyl acetate; 4-tert.-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

Esters of cycloaliphatic carboxylic acids, such as allyl 3-cyclohexylpropionate; allyl cyclohexyloxyacetate; methyl dihydrojasmonate; methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

Aromatic hydrocarbons, such as styrene and diphenylmethane;

Araliphatic alcohols, such as benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

Esters of araliphatic alcohols and aliphatic carboxylic acids, such as benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate; araliphatic ethers such as for example 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaldehyde dimethyl acetal; phenylacetaldehyde glyceryl acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

Aromatic and araliphatic aldehydes, such as benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert.-butylphenyl)propanal; 3-(4-tert.-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

Aromatic and araliphatic ketones, such as acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert.-butyl-1,1-dimethyl-4-indanyl methyl ketone;

1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

Aromatic and araliphatic carboxylic acids and esters thereof, such as acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

Nitrogen-containing aromatic compounds, such as 2,4,6-trinitro-1,3-dimethyl-5-tert.-butylbenzene; 3,5-dinitro-2,6-dimethyl-4-tert.-butylacetophenone; cinnamonitrile; 5-phenyl-3-methyl-2-pentenenitrile; 5-phenyl-3-methylpentanenitrile; methyl anthranilate; methyl N-methylanthranilate; Schiff bases of methyl anthranilate with 7-hydroxy-3,7-dimethyloctanal; 2-methyl-3-(4-tert.-butylphenyl)propanal or 2,4-dimethyl-3-cyclohexenecarbaldehyde; 6-isopropylquinoline; 6-isobutylquinoline; 6-sec.-butylquinoline; indole; skatole; 2-methoxy-3-isopropylpyrazine; 2-isobutyl-3-methoxypyrazine;

Phenols, phenyl ethers and phenyl esters, such as estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

Heterocyclic compounds, such as 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one; and Lactones, such as 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

Other suitable fragrance oils are those listed in U.S. Patent Application Publication Nos. 2012/0107529 and 2013/0202788, and U.S. Pat. No. 7,294,612, which are incorporated by reference in their entirety herein.

The compositions of the invention may also be formulated as insect repellant compositions that provide extended release of an insect repellant oil. The compositions may comprise any insect repellant oil or oils, including, for example, essential oils of citronella, catnip, and lavender; neem seed oil, and soy oil. Other suitable insect repellant oils are those listed in PCT Application Publication No. WO/2003013243; U.S. Pat. No. 8,501,205; and U.S. Published Application No. 2013/0084347, which are incorporated by reference in their entirety herein. These include, without limitation, lemongrass oil, rose geranium oil, lemon *eucalyptus* oil, and *litsea cubeba* oil, camphor, mineral oil, and geranium oil. As used herein, the term "fragrance oil" is intended to include insect repellant oils.

Oil Phase

The antiperspirant compositions also comprise an oil phase, typically in an amount from about 0.1 to about 20%, more typically from about 1 to about 10%, or from about 2 to about 8% by weight. The oil phase has a low content of unsaturated hydrocarbons. The oil phase typically comprises one or more vegetable triglyceride oils collectively having 75% or more, 80% or more, 85% or more, 90% or more, or 95% or more of the fatty acids being saturated fatty acids. In one embodiment, the oil phase comprises from about 2-6% by weight (e.g., about 4% by weight) of such one or more vegetable triglyceride oils having a high saturated fatty acid content. In one embodiment, the oil phase comprises coconut oil and/or palm kernel oil, as opposed to the conventional sunflower seed oil. In one embodiment, at least 50%, at least 60%, at least 70%, at least 80%, at least 90%, at least 95%, or at least 98% of the oil phase is comprised of coconut oil and/or palm kernel oil.

Unexpectedly, it has been found that an oil phase comprising one or more vegetable triglyceride oils collectively having 75% or more saturated fatty acids and having low levels of or no unsaturated fatty acids, provide significantly longer lasting fragrance on storage as compared with compositions comprising vegetable triglyceride oils collectively having less than 75% saturated fatty acids (e.g., sunflower seed oil). While not wishing to be bound by theory, it is believed that the fewer number of double bonds in highly saturated oils (e.g., coconut oil) results in less susceptibility to auto oxidation by free radicals as compared with oils containing high amounts of unsaturated fatty acids. The conventional oil used in antiperspirants, sunflower seed oil, is comprised of approximately 25% monounsaturated fatty acid chains and approximately 60% polyunsaturated fatty acid chains (i.e., 85% unsaturated fatty acid content). Such triglyceride oils are believed to be subject to thermally catalyzed auto oxidation. The auto oxidation process is thought to proceed by a free radical chain mechanism and creates hyper-peroxides and other free radicals which propagate the process. Hyper-peroxides decompose and form aldehydes and ketones which alter fragrance character, block perceived fragrance intensity, and create off odors in the base. Heavy metals and other raw ingredients are believed to accelerate this process. On the other hand, coconut oil has high amounts of saturated fatty acids (i.e., 75% or more saturated fatty acids). Such oils having fewer double bonds are believed to be much less susceptible to auto oxidation by free radicals.

Typically the fatty acid content of the oil phase comprises at least 75% (or at least 80%, 85%, 90%, 95%, or 98%) of fatty acids having a chain length of C16 or less. By nature, many naturally occurring triglycerides having a high content of fatty acids of C16 or less have relatively low degrees of unsaturation compared to those with a high content of fatty acids having a chain length longer than C16. In some embodiments, the oil phase of the compositions comprises less than 5%, 4%, 3%, 2%, is substantially free of (i.e., less than 1% by weight), or is free of, oils having a relatively high unsaturated fatty acid content (i.e., greater than 25%), such as sunflower oil, sunflower seed oil, rapeseed oil, corn oil, cottonseed oil, flaxseed oil, olive oil, safflower oil, soybean oil, canola oil, peanut oil, sesame oil, almond oil, castor oil, and combinations thereof.

The one or more vegetable triglyceride oils having a high saturated fatty acid content (i.e., 75% or more) present in the composition of the invention may advantageously provide benefits such as skin moisturizing, lessening the whitening effect left behind by residual antiperspirant actives of antiperspirant compositions, reducing skin irritancy and/or darkening, and evening out skin tone.

In some embodiments, fatty acids in addition to those found in the plant oils may be added to the compositions. Examples of such additional fatty acids include without limitation stearic acid, caprylic acid, lauric acid, myristic acid, palmitic acid, arachidic acid, behenic acid, lignoceric acid, or cerotic acid. However, where such additional fatty acids are included, it will be in amount of less than 6%, 5%, 4%, 3%, 2%, or 1% by weight of the composition. In some embodiments, the compositions are substantially free (i.e., <1%) or free of such additional fatty acids.

Antiperspirant Actives

The composition may also comprise one or more antiperspirant actives. Preferably, the one or more antiperspirant actives are aluminum salt-based or aluminum/zirconium salt-based. Examples of suitable antiperspirant agents include aluminium chloride, aluminium sulphate, aluminium chlorohydrate, aluminum zirconium trichlorohydrate, aluminum zirconium tetrachlorohydrate, aluminum zirconium pentachlorohydrate, and aluminum zirconium octachlorohydrate basic aluminium bromide, zirconyl chloride; zirconyl hydroxide; zirconyl chlorohydrate complexes of aluminium hydroxide, zirconyl chloride and aluminium chlorohydrate; complexes of aluminium hydroxide, zirconyl chlorohydrate, and aluminium chlorohydrate; complexes of dihydroxyaluminium glycinate, zirconyl chloride and/or zirconyl chlorohydrate and aluminium chlorohydrate; complexes of zirconyl chloride and/or zirconyl chlorohydrate and aluminium chlorohydrate; complexes of zirconyl chloride and/or zirconyl chlorohydrate with aluminium chlorohydrate and an amino acid, such as glycine; or combinations thereof. The antiperspirant actives within the invention may also comprise aluminum chloride complexes with urea. Additionally, the one or more antiperspirant actives may comprise calcium chloride and/or other metal halide salts capable of reducing body sweating. Preferably, the antiperspirant actives are aluminium zirconium chlorohydrate complexes, such as aluminium zirconium tetrachlorohydrate and aluminium zirconium pentachlorohydrate. More preferably, such complexes are combined with glycine (e.g., aluminium zirconium trichlorohydrex-gly, aluminium zirconium tetrachlorohydrex-gly, aluminum zirconium pentachlorohydrex-gly, aluminum zirconium octachlorohydrex-gly).

Typically the antiperspirant active is present in an amount from about 1 to about 25%, from about 5 to 25%, from about 5 to 15%, or from about 10 to 25%, the one or more antiperspirant actives measured as anhydrous solids. When the composition comprises an aluminum antiperspirant active, it is preferably present in an amount from 5 to 25%. When the composition comprises an aluminum zirconium antiperspirant active, it is preferably present in an amount from about 5 to 20%. In one embodiment, at least one aluminum zirconium antiperspirant active is present in an amount of 5-15% by weight based on the weight of the anhydrous aluminum zirconium).

Emulsifiers

The invention may further comprise one or more suitable emulsifiers. The one or more emulsifiers are typically present, individually or collectively, in an amount from about 0.1 to 10% by weight (e.g., about 0.5%, 1%, 2%, 3%, 4%, 5%, 6% or 7%) by weight of the composition. The one or more emulsifiers may be ionic, zwitterionic, or nonionic. Suitable emulsifiers include those of the polyethoxylated type (e.g., polyoxyethylene ethers or esters), polydiorganosiloxane-polyoxyalkylene block copolymers (e.g., dimethicone copolyol), Steareth-20, Steareth-21, fatty alcohols (e.g., Cetearyl Alcohol), Polyoxethylene sorbitan fatty acid esters (i.e., polysorbates), and Hydrogenated Castor Oil, to name a few.

Additional emulsifiers are provided in the INCI Ingredient Dictionary and Handbook 11th Edition 2006, the disclosure of which is hereby incorporated by reference. The emulsifiers may have a high or low HLB. In a preferred embodiment, the composition comprises a combination of nonionic emulsifiers each having an HLB between 3-17, in such a ratio as to give a final HLB between 6-12. In one embodiment, the one or more emulsifiers are present in an amount of 1-5% by weight. In another embodiment, the compositions comprise a low HLB emulsifier (i.e., HLB value of 1-6) in amount of 0.1-5% by weight, and a high HLB emulsifier in an amount of 0.1-5% by weight.

Polyols

The compositions of the invention typically comprise a polyol, for example in an amount from about 1% to about 20%, or from about 2% to about 15% by weight of the composition, more typically in an amount from about 2% to about 5% by weight of the composition. In one embodiment, the polyol (e.g., glycerin) will comprise about 3-5% by weight of the composition. Suitable polyols for inclusion in the compositions include, without limitation, $C_{2-6}$ polyols such as ethylene glycol, propylene glycol, butylene glycol, hexylene glycol, sorbitol, diethylene glycol, and glycerin. In one embodiment, the polyol comprises glycerin. The compositions may also comprise humectants (in addition to the polyol) such as polyols (e.g., glycols), including without limitation, glycerin, propylene glycol, ethoxydiglycol, butylene glycol, pentylene glycol, hexylene glycol, caprylyl glycol, and the like. These may be added in amount, for example, from about 0.001 to about 5% by weight of the composition.

Alcohols

In one embodiment, the compositions of the invention may be alcohol-free or substantially alcohol-free.

In other embodiments, the compositions of the invention may also typically comprise an alcohol (e.g., a fatty alcohol), for example in an amount from about 0.1% to about 5%, or more typically comprise from about 1% to about 5% by weight of the composition. In one embodiment, the alcohol comprises about 1% by weight of the composition. Any alcohol can be used in the compositions of the invention, but preferably the alcohol is a $C_{6-24}$ fatty alcohol, such as stearyl alcohol, cetyl alcohol, or mixtures thereof.

The weight ratio of the polyol to the alcohol will typically be from about 10:1 to about 1:5, or about 5:1 to about 1:2, about 4:1 to about 1:2, from about 3:1 to about 1:1, or from about 2:1 to about 1:1. Preferably, the weight ratio of polyol to alcohol will be 4:1.

Film Formers

The compositions may include natural or synthetic film-forming polymers to impart benefits, for example, resistance to humid conditions. Suitable polymeric film formers include polyolefins, silicone polymers (e.g., dimethicones, dimethiconols, amodimethicones, silicone resins, etc.), (meth)acrylates, alkyl (meth)acrylates, polyurethanes, fluoropolymers, silicone polyurethanes, and silicone acrylates such as acrylates/dimethicone copolymers. In some embodiments, it may be desirable to add a hydrophilic or water-soluble film former (e.g., cellulosics, polysaccharides, polyquaterniums (such as polyquaternium-37 (INCI), etc.) to the composition to improve spreading, emulsion stability, aesthetic look and feel, etc. Elastomers formed from ethylene, propylene, butylene, and/or styrene monomers may also be useful. Typically the film formers are present in an amount of from about 0.0001% to about 25% by weight of the composition, including amounts from about 0.001-20% by weight, or 0.01-10% by weight, or from 0.05-5% by weight, or from 0.1-1% by weight.

Colorants and Fillers

The compositions may further comprise one or more colorants or fillers. Suitable colorants colorants and fillers include those such as dyes, pigments and lakes. As used herein, the term "pigments" embraces lakes and fillers such as talc, calcium carbonate, etc. Exemplary inorganic pigments include, but are not limited to, inorganic oxides and hydroxides such as magnesium oxide, magnesium hydroxide, calcium oxide, calcium hydroxides, aluminum oxide, aluminum hydroxide, iron oxides ($\alpha$-$Fe_2O_3$, $\gamma$-$Fe_2O_3$, $Fe_3O_4$, FeO) and iron hydroxides including red iron oxide, yellow iron oxide and black iron oxide, titanium dioxide, titanium lower oxides, zirconium oxides, chromium oxides, chromium hydroxides, manganese oxides, manganese hydroxides, cobalt oxides, cobalt hydroxides, cerium oxides, cerium hydroxides, nickel oxides, nickel hydroxides, zinc oxides and zinc hydroxides and composite oxides and composite hydroxides such as iron titanate, cobalt titanate and cobalt aluminate and the like. The inorganic oxide particles may be selected from, for example, silica, alumina, zinc oxide, iron oxide and titanium dioxide particles, and mixtures thereof. However, it is preferable that the selected pigments do not comprise mica.

Additional exemplary color additive lakes include, for example: D&C Red No. 19 (e.g., CI 45170, CI 73360 or CI 45430); D&C Red No. 9 (CI 15585); D&C Red No. 21 (CI 45380); D&C Orange No. 4 (CI 15510); D&C Orange No. 5 (CI 45370); D&C Red No. 27 (CI 45410); D&C Red No. 13 (CI 15630); D&C Red No. 7 (CI 15850:1); D&C Red No. 6 (CI 15850:2); D&C Yellow No. 5 (CI 19140); D&C Red No. 36 (CI 12085); D&C Orange No. 10 (CI 45475); D&C Yellow No. 19 (CI 15985); FD&C Red #40 (CI#16035); FD&C Blue #1 (CI#42090); FD&C Yellow #5 (CI#19140); or any combinations thereof.

The colorants and fillers may be present in the composition in an amount of from about 0.0001% to about 25% by weight of the composition, including amounts from about 0.001-20% by weight, or 0.01-10% by weight, or from 0.05-5% by weight, or from 0.1-1% by weight.

Carriers

The compositions may further include any suitable cosmetically acceptable carrier in an amount of from about 1 to 99% or from about 50 to 90%, from about 60 to 90%, from about 70 to 90%, or from about 80 to 90%, by weight.

The compositions may be anhydrous, substantially anhydrous, or may comprise water. By "substantially anhydrous" is meant that no water is intentionally added to the composition, and only those amounts of water typically associated with the raw ingredients (e.g., due to the hygroscopic nature of glycerin and alcohol) are included. More typically, the compositions are hydrous and comprise water in a mount sufficient to make the composition.

Other cosmetically or dermatologically acceptable vehicles may be used, such as an ethanolic vehicle, silicone (e.g., cyclomethicone, dimethicone, etc.), hydrocarbon (e.g., petrolatum, isododecane, etc.), ester oil (isopropyl myristate, myristyl myristate) or the like. The vehicle may be anhydrous and may comprise oils, such as dimethicones, hydrocarbons (e.g., isododecane), petrolatum, ester oils, and the like. The vehicle may further comprise an emulsifier, gelling agent, structuring agent, rheology modifier (e.g., a thickener), film former, or the like. The vehicle may be in the form of, for example, a serum, a cream, a lotion, a gel, or a stick, and may comprise an emulsion (e.g., water-in-oil, oil-in-water, water-in-silicone, silicone-in-water, polyol-in-silicone, silicone-in-polyol emulsion, etc.), or may comprise an aqueous or The vehicle may comprise from about 25% to about 99% by weight of the composition.

Emollients

The composition may further comprise one or more emollients such as ester oils, hydrocarbon oils, silicone oils etc. Suitable emollients include ethers, isopropyl myristate, petrolatum, isopropyl lanolate, dimethicone oils, methicone oils, ester oils, mineral oils, cetyl ethylhexanoate, isopropyl isostearate, diisopropyl dimer dilinoeate, hydrocarbon oils, or any mixture thereof. Any emollient can be used in the compositions of the invention, such as those described in U.S. Pat. Nos. 8,545,821 and 8,580,283, hereby incorporated by reference in its entirety. The emollients are present in an amount of from about 0.1 to 25%, from about 0.1 to 10%, or from about 0.1 to 1% by weight of the composition. In one embodiment, the composition contains emollient in the amount of 1-3%.

Preservatives

One or more preservatives conventionally used in the cosmetic/personal care fields may be included in the composition. Preferably, the preservative is from the family of quaternary ammonium salts (e.g., benzalkonium chloride, cetrimonium chloride, benzethonium chloride, etc.). The one or more preservatives may be present in a total amount of from about 0.01 to about 0.1% by weight of the total composition.

Antioxidants

The composition may comprise any antioxidant conventional for use in the cosmetic field which will not cause the fragrance oil to separate from other ingredients of the composition or otherwise contribute an off odor to the composition. Examples of antioxidants that may be used in the present compositions include compounds having phenolic hydroxy functions, such as ascorbic acid and its derivatives/esters; beta-carotene; catechins; curcumin; ferulic acid derivatives (e.g., ethyl ferulate, sodium ferulate); gallic acid derivatives (e.g., propyl gallate); lycopene; reductic acid; rosmarinic acid; tannic acid; tetrahydrocurcumin; tocopherol and its derivatives; uric acid; butylated hydroxytoluene (BHT); or any mixtures thereof. Other suitable antioxidants are those that have one or more thiol functions (—SH), in either reduced or non-reduced form, such as glutathione, lipoic acid, thioglycolic acid, thiodipropionic acid, and other sulfhydryl compounds. The antioxidant may be inorganic, such as bisulfites, metabisulfites, sulfites, or other inorganic salts and acids containing sulfur. Preferably the antioxidant comprises at least one cyclic (i.e., aryl) ring. Compositions of the present invention may comprise an antioxidant from about 0.001% to about 0.20% or from about 0.001% to about 0.1% of the total weight of the composition. In one embodiment, the composition is substantially free or free of antioxidant. In another embodiment, the composition is substantially free or free of the antioxidant BHT. In another embodiment, the composition may contain a metal ion chelator, for example EDTA.

Additional Optional Ingredients

The compositions may also optionally include one or more of anti-allergenics; anti-fungals; antiseptics; anti-irritants; anti-inflammatory agents; antimicrobials (e.g., methylchloroisothiazolinone, methylisothiazolinone, methylparaben, propylparaben, phenoxyethanol, or caprylyl glycol); anti-bacterials; and analgesics in an amount from about 0.001 weight % to about 20 weight % of the total weight of the composition.

A sunscreen may be included to protect the skin from damaging ultraviolet rays. In one embodiment, the sunscreen provides both UVA and UVB protection, by using either a single sunscreen or a combination of sunscreens. Among suitable sunscreens are avobenzone, cinnamic acid derivatives (such as octylmethoxy cinnamate), octyl salicylate, oxybenzone, octocrylene, titanium dioxide, zinc oxide, or any mixtures thereof. The sunscreen may be present from about 1% to about 30% by weight of the total composition.

Other suitable components include those agents that provide a prophylactic or therapeutic benefit to skin. Particular mention may be made of alpha-hydroxy acids, beta hydroxyl acids, ascorbic acid or Vitamin C and derivatives thereof (e.g., $C_1$-$C_8$ esters thereof); retinoids such as retinol (Vitamin A) and the esters thereof (e.g., $C_1$-$C_8$ esters, such as palmitate), and hyaluronic acid.

The compositions of the invention may optionally include any additional skin or other beauty benefit agents used in antiperspirant compositions. For example, the compositions may comprise optical modification particles (e.g., soft focus particles), waxes, vegetable oils, esters, and fatty alcohols/acids; skin penetration enhancers; conditioners; actives (e.g., botanical extracts, etc.) solvents; powers and fillers; skin plumpers (e.g., palmitoyl oligopeptide), humectants (e.g., polyols, including propylene glycol, glycerin, etc.); vitamins and vitamin derivatives (e.g., ascorbic acid, tocopherol, ascorbyl monopalmitate, tocopheryl acetate, Vitamin E palmitate etc.); alpha-hydroxy acids (e.g., glycolic acid), beta-hydroxy acids (e.g., salicylic acid); retinoids (e.g., retinoic acid, all-trans-retinoic acid, retinaldehyde, retinol, and retinyl esters such as acetates or palmitates); other anti-aging ingredients (e.g., collagen stimulators, collagenase inhibitors, elastase inhibitors); depigmenting agents (e.g., TDPA, hydroquinone, kojic acid, etc.); exfoliating agents (e.g., glycolic acid, 3,6,9-trioxaundecanedioic acid, etc.); estrogen synthetase stimulating compounds (e.g., caffeine and derivatives); compounds capable of inhibiting 5 alpha-reductase activity (e.g., linolenic acid, linoleic acid, finasteride, and mixtures thereof); and barrier function enhancing agents (e.g., ceramides, glycerides, cholesterol and its esters, alpha-hydroxy and omega-hydroxy fatty acids and esters thereof, etc.), and pH adjusters (citric acid, ethanolamine, sodium hydroxide, etc.), excipients, emulsifying agents, antioxidants, surfactants, film formers, chelating agents, gelling agents, thickeners, emollients, humectants, moisturizers, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, antiallergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, lubricants, fragrances, colorants, staining agents, hypopigmenting agents, preservatives, stabilizers, pharmaceutical agents, photostabilizing agents, and mixtures thereof, to name a few. The amounts of these various substances are those that are conventionally used in the cosmetic/personal care fields to achieve their intended purposes, for example, they may constitute from about 0.001% to about 20% by weight of the total weight of the composition.

In some embodiments, the compositions may optionally include hair minimizing actives. Examples of suitable hair minimizing actives include without limitation hydrolyzed soy protein, salicylic acid, witch hazel extract, willow bark extract, or combinations thereof. Hair minimizing actives are typically present in the compositions in an amount from about 0.001-5% by weight.

In some embodiments, the compositions may optionally comprise skin lightening agents such as thiodipropionic acid (TDPA), dilauryl-TDPA, citric acid, alpha hydroxy acids, kojic acid, ascorbic acid, or ester derivatives thereof; hydroquinone, and glutathione; plant extracts (e.g., *Stenoloma chusana*, *Morinda citrifolia*, licorice, *Glycyrrhiza glabra*, arbutin, bearberry, *Chlorella vulgaris* extract, *Perilla* extract, and coconut fruit extract), or other lightening agents such as those described in US Patent Application Publication Serial No. 2004/0126344, herein incorporated in its entirety for all purposes, as well as derivatives and combinations thereof. Typically, the skin lightening agents are present in an amount from about 0.0001-20% by weight of the composition.

The compositions of the invention may optionally comprise other active and inactive ingredients typically associated with cosmetic and personal care products, including, but not limited to, excipients, fillers, emulsifying agents, antioxidants, surfactants, film formers, chelating agents, gelling agents, thickeners, and emollients. The other optional active and inactive ingredients may be present in amounts, individually or in the aggregate, from about 0.001%-20% by weight of the composition.

Other suitable additives include metal chelating agents such as EDTA or salts thereof, in an amount of from about 0.01 to 0.5% by weight of the composition.

In one embodiment, the compositions are in the form of a liquid suitable for use as a roll-on antiperspirant. In another embodiment, the compositions have a viscosity of 2,000-20,000 cps or from 5,000-10,000 cps or from 6,000-7,000 cps at 25° C.

In some embodiments, the compositions of the invention are in the form of a clear or translucent gel. The compositions may take the form of semi-solid, non-flowable, or flowable gels. In other embodiments, the compositions of the invention may be formulated as a cream, foam, stick, or spray.

The compositions of the invention may be used in any suitable antiperspirant compositions, including without limitation creams, gels, deodorants, and the like, particularly for topical administration.

The compositions of the invention are capable of retaining fragrance on storage over a longer period of time as compared to otherwise identical compositions that contain one or more vegetable triglyceride oils collectively having less than 75% saturated fatty acids. The compositions of the invention are useful for application to the human integumentary system, including, skin, lips, nails, hair, and other keratinous surfaces. As used herein, the term "keratinous surface" refers to keratin-containing portions of the human integumentary system, which includes, but is not limited to, skin (e.g., the underarms), lips, hair (including eyebrows and eyelashes, hair of the scalp, facial hair, and body hair such as hair of the arms, legs, etc.), and nails (toenails, fingernails, cuticles, etc.) of mammalians, preferably humans The composition can be applied as often as necessary to impart the desired antiperspirant effect to the skin. A composition according to the invention may achieve extended release of fragrance oil for a long-wear period such as from about 1 to about 48 hours, from about 1 to about 24 hours or from about 1 to about 12 hours.

The composition according to the invention may be suitably packaged in a container equipped to deliver the composition to the skin. The composition may be in the form of a liquid having a rheology and viscosity suitable for use with a roll-on applicator wherein the composition is communicated from the reservoir within the container to the skin via a rotatable ball, porous material, or the like. In another embodiment of the invention, a packaged personal care product is provided comprising a container in which is disposed a liquid composition according to the invention, and a roll-on applicator for delivering an amount of the composition to an integument of a user, the roll-on applicator being affixed to the container and in contact with the liquid in the reservoir. In other embodiments, packaged personal care products are provided comprising a container having a composition according to the invention contained therein, the composition being in the form of a solid or gel, and a means for advancing said composition (e.g., a turnable screw assembly) from an open orifice of said container.

EXAMPLES

Example 1

Two compositions were prepared according to the formulas in Table 1. Each formula was identical except that the control composition included 4% by weight of sunflower seed oil (having a fatty acid content wherein 85% or more are unsaturated fatty acids) (Sample A), while the inventive composition included 4% by weight coconut oil (having a fatty acid content wherein 75% or more of the fatty acids are saturated). (Sample B).

TABLE 1

| Ingredient | Sample A with Sunflower Seed Oil (%) | Sample B with Coconut Oil (%) |
|---|---|---|
| Glycerin | 4 | 4 |
| Low HLB Emulsifier (1-6) | 2.772 | 2.772 |
| High HLB Emulsifier | 0.9 | 0.9 |
| Emollient Ether | 1.65 | 1.65 |
| Coconut Oil | 0 | 4 |
| Sunflower Seed Oil | 4 | 0 |
| Aluminum zirconium active (anhydrous) | 10.25 | 10.25 |
| Preservative | 0.05 | 0.05 |
| Alcohol | 1 | 1 |
| Fragrance A | 1.5 | 1.5 |
| | qs water to 100 | qs water to 100 |

Samples A and B were stored at 4.4° C. (40° F.) as a control and 43° C. (110° F.) as an accelerated condition. A third composition comprising the same ingredients of Composition A (sunflower seed oil) plus 0.1% weight of an antioxidant was also stored under the same conditions. After accelerated storage periods of one, two, and three months, the compositions were applied to skin and the fragrance character and intensity of individual samples of the three compositions was evaluated by a panel of three fragrance experts. Assessments ranged from a score of 10 (best) being full perception of original fragrance character and intensity to 1 (worst) being no perception of fragrance. The mid-value of 5 was designated as "acceptable" or "passing." Table 2 shows the unexpected benefit realized by using coconut oil as opposed to sunflower seed oil in antiperspirant compositions.

TABLE 2

| | Storage Condition | | | |
|---|---|---|---|---|
| Sample | 4.4° C. (40° F.) Control | 43° C. (110° F.) at 1 month | 43° C. (110° F.) at 2 month | 43° C. (110° F.) at 3 month |
| Sample A | 10 | 5 | 4 | 1 |
| Sample B | 10 | 8 | 6 | 5 |
| Sample A + 0.1% antioxidant | 10 | 5 | physically unstable separation | physically unstable separation |

As shown in Table 2, the fragrance character and intensity of the control formula made with sunflower seed oil degrades much faster than the formula made with coconut oil. Sample A (sunflower seed oil) became unacceptable between one and two months of storage, and had almost no trace of fragrance after being stored for three months. In contrast, Sample B (coconut oil) retained acceptable fragrance at three months storage. Furthermore, the degradation of fragrance character observed for Sample A was not slowed by the inclusion of an antioxidant (i.e. Sample C) after one month of storage. Instead, the antioxidant caused the control to become physically unstable between one and two months of accelerated storage.

Other sample formulas that may be within the scope of the present invention are shown below:

| Ingredient | |
|---|---|
| Glycerin | 4 |
| Low HLB Emulsifier (1-6) | 2.772 |
| High HLB Emulsifier | 0.9 |
| Emollient Ether | 1.65 |
| Coconut Oil | 4 |
| Sunflower Seed Oil | 0 |
| Aluminum zirconium active (anhydrous) | 10.25 |
| Preservative | 0.05 |
| Alcohol | 0-1 |
| Metal Ion Chelator (EDTA) | 0-1 |
| Fragrance A | 1.5 |
| | qs water to 100 |

The invention described and claimed herein is not to be limited in scope by the specific embodiments herein disclosed since these embodiments are intended as illustrations of several aspects of the invention. Any equivalent embodiments are intended to be within the scope of this invention. Indeed, various modifications of the invention in addition to those shown and described therein will become apparent to those skilled in the art from the foregoing description. Such modifications are also intended to fall within the scope of the appended claims. All publications cited herein are incorporated by reference in their entirety.

The invention claimed is:

1. An antiperspirant composition comprising one or more fragrance oils dispersed in an oil phase and one or more aluminum-based or aluminum/zirconium-based antiperspirant actives, said oil phase comprising one or more triglyceride oils, wherein said triglyceride oils collectively have a saturated fatty acid content of at least 75%;
   wherein said composition comprises from about 0.1 to about 3% of said one or more fragrance oils by weight of the composition and from about 1 to about 20% of said one or more triglyceride oils by weight of the composition, wherein said composition is in the form of an oil-in-water emulsion; and wherein said composition is a liquid having a viscosity below 7000 cps at 25° C.

2. The antiperspirant composition of claim 1, wherein said triglyceride oils collectively have a saturated fatty acid content of at least 85%.

3. The antiperspirant composition of claim 1, wherein said triglyceride oils collectively have a saturated fatty acid content of at least 90%.

4. The antiperspirant composition of claim 1, wherein the fatty acid content of said triglyceride oils comprises at least 75% fatty acids having a chain length of C16 or less.

5. The antiperspirant composition of claim 1, wherein said one or more triglyceride oils comprise coconut oil.

6. The antiperspirant composition of claim 1, wherein said oil phase comprises less than 5% of a triglyceride oil selected from the group consisting of sunflower seed oil, rapeseed oil, corn oil, cottonseed oil, flaxseed oil, olive oil, safflower oil, soybean oil, canola oil, peanut oil, sesame oil, almond oil, castor oil, and combinations thereof.

7. The antiperspirant composition of claim 1, wherein said one or more antiperspirant actives is selected from the group consisting of an aluminum salt, an aluminum/zirconium salt, an aluminum glycol complex, an aluminum/zirconium glycol complex, or combinations thereof.

8. The antiperspirant composition of claim 1, further comprising a polyol.

9. The antiperspirant composition of claim 8, wherein said polyol comprises glycerol.

10. The antiperspirant composition of claim 1 comprising:
(a) from about 0.1 to about 3% of one or more fragrance oils;
(b) from about 1 to about 20% coconut oil;
(c) from about 5 to about 25% of an aluminum-based or aluminum/zirconium-based antiperspirant active;
(d) from about 2 to about 20% polyol;
(e) from about 50 to about 90% water; and
(f) from about 1 to about 7% of one or more emulsifiers.

11. The antiperspirant composition of claim 10 wherein said one or more emulsifiers collectively have an HLB value of between 6-12.

12. The antiperspirant composition of claim 1, further comprising one or more antioxidants.

13. The antiperspirant composition of claim 1, wherein said one or more antioxidants comprise a water-insoluble sterically hindered phenolic antioxidant.

14. The antiperspirant composition of claim 1, wherein the composition contains one or more hair minimizing actives.

15. The antiperspirant composition of claim 1, wherein the composition contains one or more skin lightening agents.

16. The antiperspirant composition of claim 12, wherein the total amount of said one or more antioxidants is ≤0.20% by weight of the composition.

17. The antiperspirant composition of claim 1, wherein the composition comprises from about 2 to about 20% polyol by weight of the composition and from about 50 to about 90% water by weight of the composition.

* * * * *